United States Patent [19]

Imaki et al.

[11] Patent Number: 5,294,723

[45] Date of Patent: Mar. 15, 1994

[54] SALTS OF GLUCOPYRANOSE DERIVATIVES AND ITS INTERMEDIATE

[75] Inventors: Katsuhiro Imaki; Shinsuke Hashimoto; Hirohisa Wakatsuka, all of Osaka, Japan

[73] Assignee: Ono Pharmaceutical Co., Ltd., Osaka, Japan

[21] Appl. No.: 10,163

[22] Filed: Jan. 28, 1993

[30] Foreign Application Priority Data

Jan. 31, 1992 [JP] Japan .................................. 4-42185
May 22, 1992 [JP] Japan ................................. 4-155913

[51] Int. Cl.$^5$ .......................................... C07D 309/10
[52] U.S. Cl. ................................................ 549/417
[58] Field of Search ..................................... 549/417

[56] References Cited

U.S. PATENT DOCUMENTS 4,925,929  5/1990  Toda et al. ........................ 536/4.1

OTHER PUBLICATIONS

Agric. Biol. Chem., 48 (1), 251–252, 1984, "Synthesis of Biologically Active, Novel Monosaccharide Analogs of Lipid A", Makoto Kiso et al.

Primary Examiner—Nicky Chan
Attorney, Agent, or Firm—Sughrue, Mion, Zinn, Macpeak & Seas

[57] ABSTRACT

A salt of glucopyranose derivative of the formula (I)

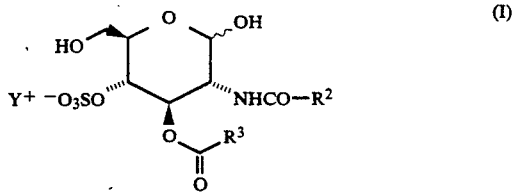

(I)

wherein
$R^2$ is

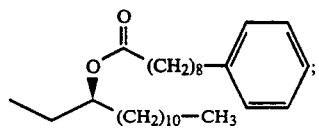

$R^3$ is

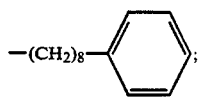

$Y^+$ is sodium ion or tris(hydroxymethyl)methylammonium ion;
and a glucopyranose derivative of the formula (II)

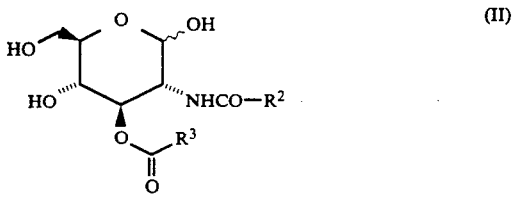

(II)

wherein all the symbols are the same meaning as hereinbefore defined, is an important intermediate for the preparation of compound of the formula (I).

1 Claim, No Drawings

SALTS OF GLUCOPYRANOSE DERIVATIVES AND ITS INTERMEDIATE

SUMMARY

This invention is related to a selective invention of ones described in the specification of the European Patent Publication No. 226381.

More particularly, this invention is related to novel salts of a glucopyranose derivative of the formula (I)

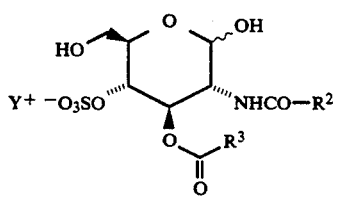

wherein
R² is

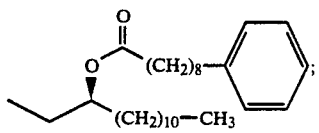

R³ is

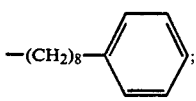

Y⁺ is sodium ion or tris(hydroxymethyl)methylammonium ion; which has a lipid A-like activity.

Further, this invention is related to a glucopyranose derivative of the formula (II)

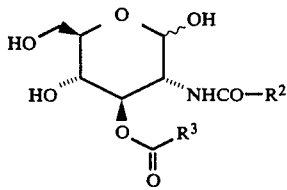

wherein all the symbols are the same meaning as herein before defined, which is useful as an intermediate of pharmaceutical agents.

BACKGROUND OF THE INVENTION

Gram-negative germs (e.g. cholera germs, salmonella germs, colon bacillus) have substances known as lipopolysaccharides (abbreviated as LPS hereafter) on the outer cell membrane, and it is considered that such substances induce endotoxin shock.

It is known that LPS have various bioactivities including fetal toxicity; this is why it is so named on endotoxin. For example, LPS have an enhancing activity of immunity which is a defensive system of a host (macrophage-activating action, B cell mitogenic activity, producing activity of non-specific antibody, enhancing activity of cellular immunity, etc.) and anti-tumor activity (interferon-inducing activity, TNF (tumor necrosis factor)-inducing activity etc.), besides a pyrogenetic activity and a hemorrhage activity. Especially, LPS is effective as a non-specific immunity agent to any antigens. LPS also has an action specifically inducing hemorrhage necrosis of tumor cells by its TNF-inducing activity, and therefore, can be useful as an anti-tumor agent.

Furthermore, its inducing activity of interleukin-1 or of interferon makes LPS useful as not only agent for enhancing immunity but also anti-tumor agent by stimulating natural killer activity.

It is known that the active center of LPS is a disaccharideamine, called lipid A, and may patent applications on derivatives of lipid A have been already filed.

RELATED ARTS

The compounds of the formula (A)

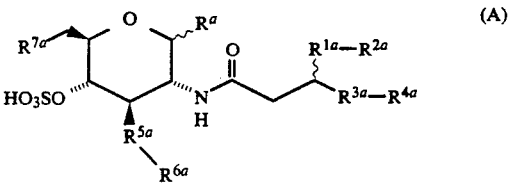

wherein
R$^a$ is hydrogen atom, hydroxy or C1-4 alkoxy;
R$^{1a}$ is single bond or C2-20 oxycarbonylalkyl;
R$^{2a}$ and R$^{6a}$ each, independently, is hydrogen atom or group of the formula

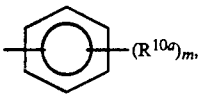

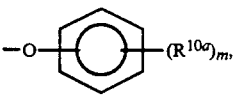

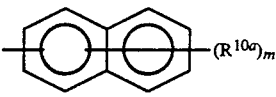

or

(wherein each R$^{10a}$ is hydrogen atom, C1-7 alkyl or alkoxy, or halogen atom; m is 1-3);
R$^{3a}$ is C1-20 alkylene;
R$^{4a}$ is hydrogen atom or group of the formula

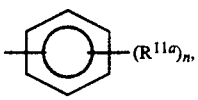

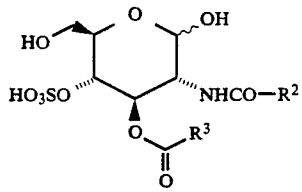

(Aa)

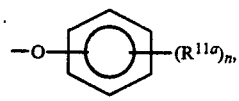

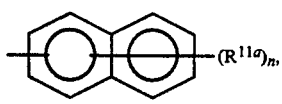

or

(wherein each $R^{11a}$ is hydrogen atom, C1-7 alkyl or alkoxy, or halogen atom; n is 1-3);

$R^{5a}$ is C2-20 oxycarbonylalkyl;

$R^{7a}$ is hydrogen atom or hydroxy;

with the proviso that, all of $R^{2a}$, $R^{4a}$ and $R^{6a}$ are not hydrogen atoms at the same time, and salts thereof, as compounds achieving the above purpose, have been already proposed in the European Patent Publication No. 226381.

2-Deoxy-2-[(3S)-(9-phenylnonanoyloxy)tetradecanoyl]amino-3-O-(9-phenylnonanoyl)-4-O-sulfo-D-glucopyranose of the formula (Aa)

wherein
$R^2$ is

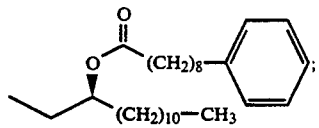

$R^3$ is

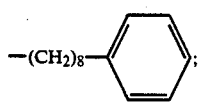

is specifically disclosed in Example 1(c) in the above patent specification.

It is described in the specification of the European Patent Publication No. 226381, that a pharmaceutical agent of the formula (Aa) may be prepared by the following Scheme 1.

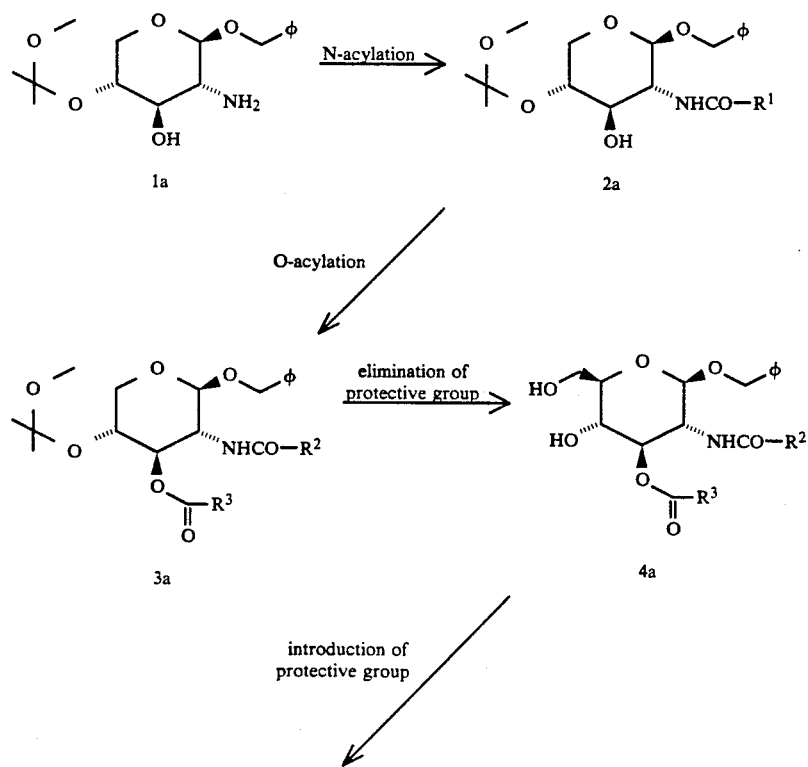

Scheme 1

-continued
Scheme 1

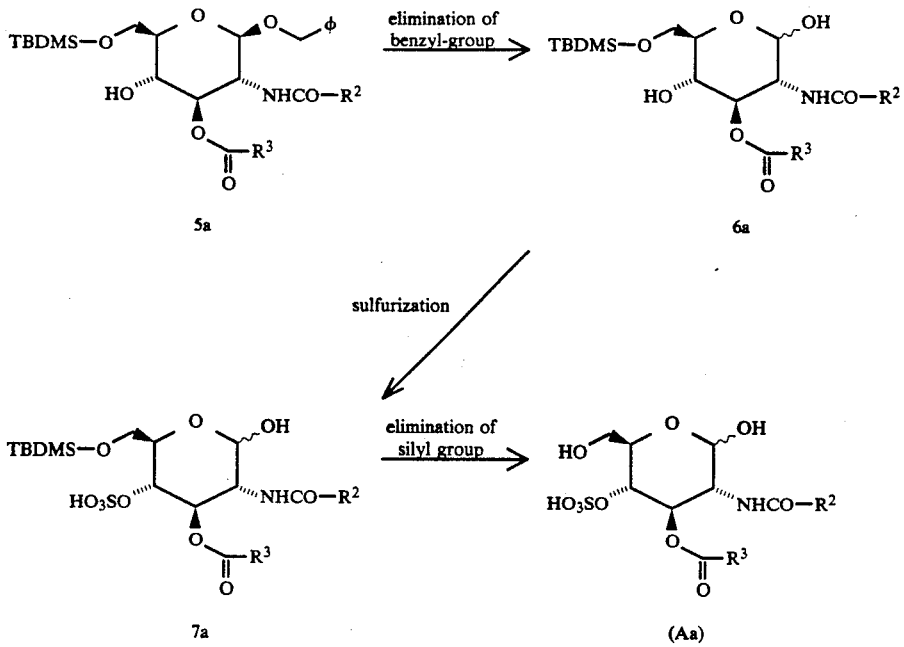

7a → (Aa)

In the scheme, R¹ is the group of the formula:

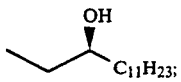

φ is phenyl;
TBDMS is t-butyldimethylsilyl;
and the other symbols are the same meaning as hereinbefore defined.

The compound of the formula 1a may be prepared in 9 steps by methods known per se from the compound of the formula 8a (being on the market)

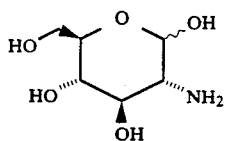

(see Agric. Biol. Chem., 48 (1), 251 (1984)).

PROBLEM IN RELATED ARTS

The glucopyranose derivative of the formula (Aa) has sufficient pharmacological activity to use as a pharmaceutical agent, but it also has the defect that its solubility for injectable solvents is very poor. Therefore, it was difficult to develop this compound as a pharmaceutical agent.

Further, as shown in Scheme 1, the conventional method requires 9 steps from stating material 8a to obtain the starting material 1a, and therefore, costs much because the starting material 1a in the method is β-D-glucopyranoside which is a particular sugar.

MEANS TO SOLVE THE PROBLEM

The present inventors have carried out their investigation for the purpose of improving the solubility or decreasing the preparation cost of the glucopyranose derivative of the formula (Aa).

As a result, it has been revealed that the compound of the formula (Aa) was not obtained as a free acid, but really obtained as a mixture of metal salts thereof.

The metals are calcium, sodium and magnesium, and the final product is not represented by the formula (Aa), but represented by the formula (B)

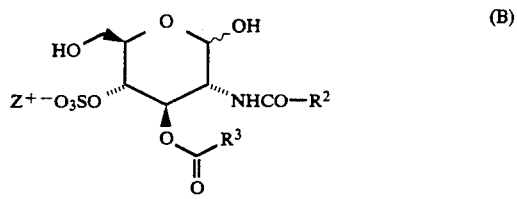

wherein $Z^+$ is a mixture of calcium ion, sodium ion and magnesium ion and the other symbols are the same meaning as hereinbefore defined.

It was confirmed later on that these metals came from impurity in silica gel for purification.

The present inventors have attempted to prepare various salts thereof in order to improve the solubility for the solvent.

Consequently, the present inventors have found that in salts of the compound of the formula (Aa), its sodium salt and tris salt (tris(hydroxymethyl)methylamine salt) have very good solubility for the solvent for the administration, compared with the mixture of salts of the formula (B) (prepared by the process described in the specification of the European Patent Publication No. 226381) and calcium salt of the compound of the formula (Aa), and have accomplished the present invention.

No specific preparation example of sodium and tris salts of the glucopyranose derivative of the formula (I) is disclosed in the specification of the European Patent Publication No. 226381, and therefore, such salts are quite novel substance prepared now for the first time. Further, it cannot be predicted that these salts possess very good solubility compared with the other salt and the fact has found for the first time.

Energetic investigations have also been carried out in order to discover industrially useful process for the preparation by using α-D-glucopyranoside of general sugar as starting material, and the present inventors have found new process depicted in Scheme 2 below. The compound of the formula (VI) in Scheme 2 corresponds to that of the formula 6a in Scheme 1. Therefore, Scheme 2 leads to a reduction of one step and decrease of preparation cost.

of the European Patent Publication No. 226381, and therefore, it is quite novel compound.

DISCLOSURE OF THE INVENTION

The present invention is related to salts of the glucopyranose derivative of the formula (I)

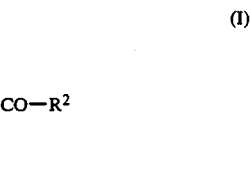

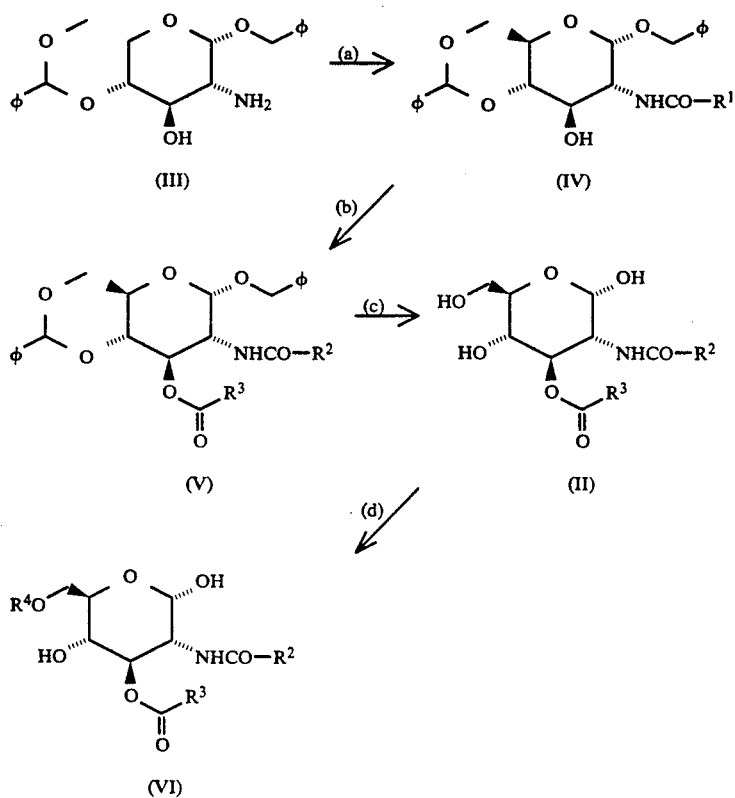

In the scheme, $R^4$ is hydroxy-protecting group which can be eliminated under an acidic condition, such as t-butyldimethylsilyl, trimethylsilyl, etc. and the other symbols are the same meaning as hereinbefore defined.

The starting material of the formula (III) in Scheme 2 may be prepared in 3 steps by methods known per se from the compound of the formula (VII) (being on the market)

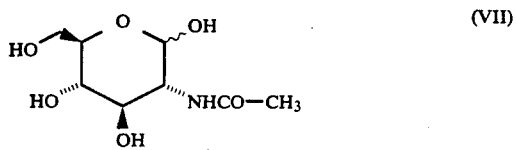

(see Liebigs Ann. Chem., 37 (1986)). Consequently, the number of steps decreases greatly and it leads to the decrease of preparation costs. There is no description of the intermediate of the formula (II) in the specification wherein
$R^2$ is

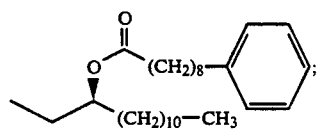

$R^3$ is

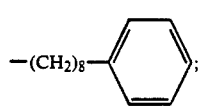

$Y+$ is sodium ion or tris(hydroxymethyl)methylammonium ion;

Throughout the specification including claims, wavy line indicates α-configuration, β-configuration or the mixture thereof.

Further this invention is related to a glucopyranose derivative of the formula (II)

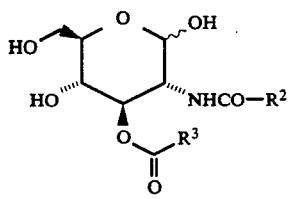
(II)

wherein each symbols are the same meaning as hereinbefore defined, which is important as an intermediate of pharmaceutical agents.

PROCESSES OF THE PREPARATION OF THE COMPOUNDS OF THE PRESENT INVENTION

The compounds of the present invention of the formula (I) may be prepared, for example, by the following methods:

1) Method of subjecting the compound of the formula (VI) to a series of (i) sulfurization→(ii) salt-exchange reaction, if desired→(iii) the elimination of hydroxy-protecting group→(iv) salt-exchange reaction, 2) Method of subjecting a purified mixture of the salts to salt-exchange by using ion-exchange resin, or 3) Method of converting all of purified mixture of the salts into calcium salt once, and then subjecting calcium salt thus obtained to salt-exchange by using ion-exchange resin.

The method 1) may be carried out according to the following Scheme 3.

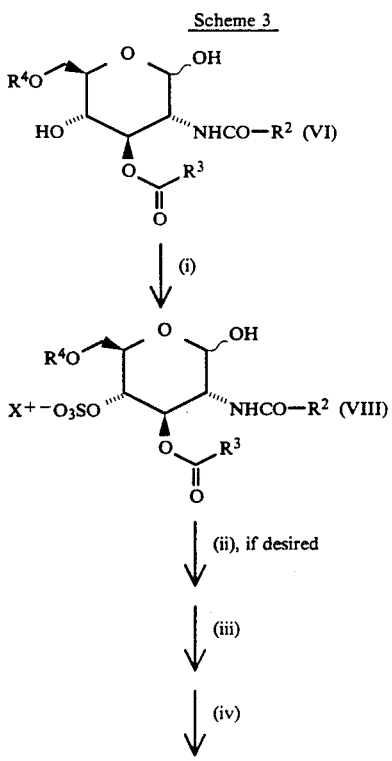

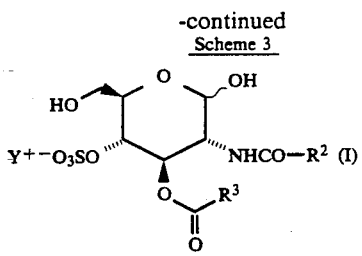

wherein $X^+$ is pyridinium ion, triethylammonium ion, dimethylanilinium ion or dimethylpyridinium ion and the other symbols are the same meaning as hereinbefore defined.

Explaining briefly each reaction, process (i), which is sulfurization, may be carried out, for example, by using a sulfurizating agent such as sulfur trioxide pyridine complex, sulfur trioxide trimethylamine complex, etc., in the presence of a tertiary amine (e.g., pyridine, triethylamine, dimethylaniline, dimethylaminopyridine, etc.) in an inert organic solvent [halgenated hydrocarbon (e.g., methylene chloride, chloroform, carbon tetrachloride, 1,1,2,2-tetrachloroethylene, perchloroethylene, chlorobenzene, etc.), ether (e.g., tetrahydrofuran, tetrahydropyran, dioxane, dimethoxyethane, diethyl ether, diisopropyl ether, diphenyl ether, methyl ethyl ether, etc.), benzene analogues (e.g., benzene, toluene, xylene, etc.), amine (e.g., triethylamine, pyridine, methylpyridine, etc.), ketone (e.g., acetone, methyl ethyl ketone, phenyl methyl ketone, etc.), nitrile (e.g., acetonitrile, etc.), amide (e.g., hexamethylphosphoramide, dimethylformamide, dimethylimidazolidinon, etc.), ethyl acetate or the mixture of two or more of them, etc.] or without solvent at a temperature of from 0° C. to 70° C.

Process (ii) and (iv), which are salt-exchange reaction, may be carried out, for example, by treating the compound dissolved into an inert organic solvent [halgenated hydrocarbon (described above), hydrocarbon (e.g., pentane, hexane, isooctane, cyclohexane, etc.), benzene analogues (described above), ether (described above), alcohol (e.g., methanol, ethanol, isopropanol, etc.), ketone (described above), nitrile (described above), ethyl acetate or the mixture of two or more of them, etc.] with an aqueous solution containing sodium or tris(hydroxymethyl)methylammonium ion. Alternatively, it also may be carried out by using ion-exchange resin as hereinafter described.

Process (iii), which are the elimination of hydroxy-protecting group, may be carried out, for example, by using an organic acid (e.g., acetic acid, p-toluenesulfonic acid, trichloroacetic acid, oxalic acid, etc.), or an inorganic acid (e.g., hydrochloric acid, sufuric acid, phosphoric acid, hydrobromic acid, etc.) or the mixture of them, in the presence of water in a water-miscible organic solvent [ether (described above), alcohol (described above), ketone (described above), nitrile (described above), sulfoxide (e.g., dimethylsulfoxide, etc.), amide (described above) or the mixture of two or more of them, etc.] at a temperature of from 0° C. to 90° C.

The compound of the formula (I) the obtained may also, if desired, purified by, for example, recrystallization, reversed phase column chromatography, ion-exchange resin, etc.

The compound of the formula (VI) may be prepared by the method described in the specification of the European Patent Publication No. 226381 or in the Scheme 2 as hereinbefore described.

The method 2) of subjecting the mixture of the salts of the formula (B) (i.e., a mixture of calcium, sodium and magnesium salts) to salt-exchange by using ion-exchange resin, may be carried out by treating the mixture of salts of the formula (B) (prepared by the process described in the specification of the European Patent Publication No. 226381, or method of subjecting the compound of the formula (VI) to a series of the reaction of (i) sulfurization→(ii) salt-exchange reaction→(iii) purification by normal silica gel column chromatography), using neutral cation-exchange resin (—$SO_3Na$ type, etc.) or acidic-exchange resin (—$SO_3H$ type, etc.) treated with an aqueous solution containing a corresponding ion (e.g., aqueous solution of sodium hydroxide or tris, etc.).

The method 3) of converting all of purified mixture of the salts of the formula (B) (i.e., a mixture of calcium, sodium and magnesium salts) into calcium salt once, and then subjecting to salt-exchange by using cation-exchange resin, may be carried out, for example, by treating the mixture of salts (prepared by the process described in the specification of the European Patent Publication No. 226381, or method of sujecting the compound of the formula (VI) to a series of the reaction of (i) sulfurization→(ii) salt-exchange reaction→(iii) purification by normal silica gel column chromatography), using column chromatography on silica gel treated with an aqueous solution containing calcium ion (e.g., an aqueous solution of calcium chloride, etc.) to convert into calcium salt, and then treating by using cation-exchange resin as described in method 2).

After these procedure, the compound thus obtained, if desired, may be further purified by recrystallization, reversed phase column chromatography, etc.

Brief description of each reaction in the Scheme 2 are as follows:

Process (d), which is the introduction of a protecting group (t-butyldimethylsilyl group) into hydroxy group, may be carried out, for example, by using t-butyldimethysilyl halide in the presence of a base (e.g., pyridine, triethylamine, dimethylaniline, dimethylaminopyridine, etc.) in an inert organic solvent [halogenated hydrocarbon (described above), ether (described above), hydrocarbon (described above), amine (described above), sulfoxide (described above), ketone (described above), nitrile (described above), amide (e.g., hexamethylphosphoramide, etc.), ethyl acetate or the mixture of two or more of them, etc.] at a temperature of from $-10°$ C. to $60°$ C.

The hydrogenation of process (c) is known per se, and may be carried out, for example, in an inert solvent [ether (described above), alcohol (described above), benzene analogues (described above), ketone (described above), nitrile (described above), amide (described above), water, ethyl acetate, acetic acid or the mixture of two or more of them, etc.], in the presence of a catalyst of hydrogenation (e.g., palladium on activated carbon, palladium black, palladium, palladium hydroxide on carbon, platinum oxide, nickel, Raney nickel (registered trade mark) etc.), in the presence or absence of an inorganic acid (e.g., hydrochloric acid, sulfuric acid, hypochlorous acid, boric acid, tetrafluoroboric acid, etc.) or an organic acid (e.g., acetic acid, p-toluenesulfonic acid, oxalic acid, trifluoroacetic acid, formic acid, etc.), at ordinary or additional pressure under an atmosphere of hydrogen, at a temperature of from $0°$ to $200°$ C. When using an acid, its salt may be used at the same time.

The O-acylation of process (b) is known per se, and may be carried out, for example, by (1) method using an acyl halide, (2) method using a mixed acid anhydride, (3) method using a condensing agent such as dicyclohexylcarbodiimide. (DCC), Mukaiyama reagent, etc.

Concrete description of these method are as follows:

(1) Method using an acyl halide may be carried out by reacting a carboxylic acid of the formula

$$HOOC—C_8H_{16}—\phi$$

with a halogenating agent (e.g., oxalyl chloride, thionyl chloride, etc.) in an inert organic solvent [halogenated hydrocarbon (described above), ether (described above), benzene analogues (described above), amine (described above), ketone (described above), nitrile (described above), amide (described above), ethyl acetate or the mixture of two or more of them, etc.], at a temperature of from $-20°$ C. to refluxing temperature of the solvent, and then reacting the acyl halide thus obtained, with the compound of the formula (IV) in the presence of a tertiary amine (e.g., pyridine, triethylamine, dimethylaniline, dimethylaminopyridine, etc.) in an inert organic solvent [halogenated hydrocarbon (described above), ether (described above), amine (described above), ketone (described above), nitrile (described above), amide (described above) or the mixture of two or more of them, etc.], at a temperature of from $0°$ C. to $40°$ C.

(2) Method using a mixed acid anhydride may be carried out, for example, by reacting a carboxylic acid of the formula

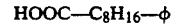
$$HOOC—C_8H_{16}—\phi$$

and an acyl halide (e.g., pivaloyl chloride, tosyl chloride, mesyl chloride, etc.) or an acid derivative (e.g., ethyl chloroformate, isobutyl chloroformate, etc.) in an inert organic solvent [halogenated hydrocarbon (described above), ether (described above), benzene analogues (described above), amine (described above), ketone (described above), nitrile (described above), amide (described above), ethyl acetate or the mixture of two or more of them, etc.] in the presence of a tertiary amine (described above) at a temperature of from $0°$ C. to $40°$ C. to give a mixed acid anhydride, and then by reacting the mixed acid anhydride thus obtained solution with a compound of the formula (IV) at the same temperature.

(3) Method using a condensing agent such as DCC, Mukaiyama reagent, etc. may be carried out, for example, by reacting a carboxylic acid of the formula:

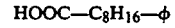
$$HOOC—C_8H_{16}—\phi$$

with a compound of the formula (IV), using a condensing agent [e.g., DCC, Mukaiyama reagent (e.g., 2-chloro-1-methylpyridinium iodide, 2-iodo-1-methylpyridinium iodide, etc.), N,N,N',N'-tetramethylchloroformamidinium chloride, 1,3-dimethyl-2-chloroimidazolinium chloride, etc.)] in the presence or absence of the tertiary amine (described above), in an inert organic solvent [halogenated hydrocarbon (described above), ether (described above), benzene analogues (described above), amine (described above), ketone (described above), nitrile (described above), amide (described above), ethyl acetate or the mixture of two or more of them, etc.] at a temperature of from 0° C. to 40° C.

The N-acylation of process (a) is known per se, and may be carried out, for example, by (1) method using a mixed acid anhydride, (2) method using a condensing agent such as DCC, Mukaiyama reagent, etc.

These methods may be carried out by the same procedure as described above for O-acylation.

Each reaction may be carried out under an atmosphere of an inert ges (e.g., argon, nitrogen, etc.), if necessary.

Products in each reaction may be provided for the next step after isolation, washing, drying and purification by steps, or without these procedures, or after only necessary procedures.

In each reaction in the present specification, products may be purified by conventional manner. For example, it may be carried out by distillation at atmospheric or reduced pressure, high performance liquid chromatography, thin layer chromatography, column chromatography, ion-exchange resin, reversed phase chromatography, washing or recrystallization.

EFFECT OF THE INVENTION

The salts of glucopyranose derivative of the formula (I) prossess as strong phamacological activity as the mixture salts of the formula (B). Further, its solubility for the solvent for the administration has been significantly improved. For example, Table 1 shows the solubility for a mixture of water-ethanol (1:1), which is considered to be a dissoluving agent in practical use.

TABLE 1

| Compound | Solubility (25° C.) Solubility (mg/ml) |
|---|---|
| Sodium salt of the present invention (Example 3) | 212 |
| Tris salt of the present invention (Example 4) | >270 |
| Mixture salt (formula (B)) (Reference example 5) | 1.5 |

As shown in Table 1, the solubility of the compound of the present invention is more than about 140 times that of the mixture salt of the formula (B).

When the compound of the formula (I) useful as pharmaceutical agents, is prepared, the method for the preparation using the compound of the formula (II) of the present invention as intermediate, is the excellent method for the industrial preparation at the following point, compared with conventional method.

i) By using the α-glucopyranoside of the formula (III) as starting material, the number of the total steps can be greatly diminished.

ii) The compounds of the formulae (III) and (IV) can be purified by recrystallization, and therefore, the purification process with column chromatography which is inadequate for industrial preparation, can be diminished.

iii) Both benzylidene and benzyl groups as protecting-group can be removed at onece in the process for converting the compound of the formula (V) into that of the formula (II), and therefore, one step can be diminished over the conventinal method

APPLICATION FOR PHARMACEUTICAL

For the treatment of immuno deficiencies or tumor, the compounds of the formula (I), of the present invention, may be normally administered systemically or partially, usually by oral or parenteral administration.

The doses to be administered are determined depending upon age, body weight, symptom, the desired therapeutic effect, the route of administration, and the duration of the treatment etc. In the human adult, the doses per person per dose are generally between 5 mg and 5000 mg, by oral administration, up to several times per day, and between 500 μg and 500 mg, by parenteral administration (preferable i.v.) up to several times per day.

As mentioned above, the doses to be used depend upon various conditions. Therefore, there are cases in which doses lower than or greater than the ranges specified above may be used.

Solid compositions for oral administration include compressed tablets, pills, capsules, dispersible powders, and granules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate, etc.). The compositions may also comprise, as is normal practice, additional substances other than inert diluents: e.g. lubricating agents (such as magnesium stearate etc.), disintegrating agents (such as cellulose calcium glycolate, etc.), stabilizing agents (such as lactose, etc.), and assisting agents for dissolving (such as glutamic acid, asparaginic acid etc.).

The tablets or pills may, if desired, be coated with a film of gastric or enteric material (such as sugar, gelatin, hydroxypropyl cellulose or hydroxypropylmethyl cellulose phthalate etc.), or be coated with more than two films. And further, coating may include containment within capsules of absorbable materials such as gelatin.

Liquid compositions for oral administration include pharmaceutically-acceptable solutions, emulsions, suspensions, syrups and elixirs. In such compositions, one or more of the active compound(s) is or are contained in inert diluent(s) commonly used in the art (purified water, ethanol etc.). Besides inert diluents, such compositions may also comprise adjuvants (such as wetting agents, suspending agents, etc.), sweetening agents, flavouring agents, perfuming agents, and preserving agents.

Other compositions for oral administration include spray compositions which may be prepared by known methods and which comprise one or more of the active compound(s).

Injections for parenteral administration include sterile aqueous or non-aqueous solutions, suspensions and emulsions. In such compositions, one more of active compound(s) is or are admixed with at least one of inert aqueous diluent(s) (distilled water for injection, physiological salt solution etc.) or inert non-aqueous diluent(s) (propylene glycol, polyethylene glycol, olive oil, ethanol, POLYSOLBATE80 (registered trade mark)etc.).

Injections may comprise additional other than inert diluents: e.g. preserving agents, wetting agents, emulsifying agents, dispersing agents, stabilizing agent (lactose etc.), assisting agents such as assisting agents for dissolving (arginine, glutamic acid, or amino acid such as asparaginic acid etc.).

They may be sterilized for example, by filtration through a bacteria-retaining filter, by incorporation of sterilizing agents in the compositions or by irradiation. They may also be manufactured in the form of sterile solid compositions, for example, by freeze-drying, and which may be dissolved in sterile water or some other sterile diluent(s) for injection immediately before used.

Other compositions for parenteral administration include liquids for external use, and endermic liniments, -ointment, suppositories and pessaries which comprise one or more of the active compound(s) and may be prepared by per se known methods.

REFERENCE EXAMPLE AND EXAMPLES

The following reference examples and examples are intended to illustrate, but not limit, the present invention.

The solvents in parentheses show the developing or eluting solvents and the ratios of the solvents used are by volume in chromatographic separations.

Unless otherwise specified, "NMR" was measured in a solution of $CDCl_3$, mp means melting point.

The symbols in the chemical formula are the same meaning hereinbefore defined.

REFERENCE EXAMPLE 1

Preparation of benzyl 2-((3S)-hydroxytetradecanoyl)amino-4,6-O-benzylidene-2-deoxy-α-glucopyranoside

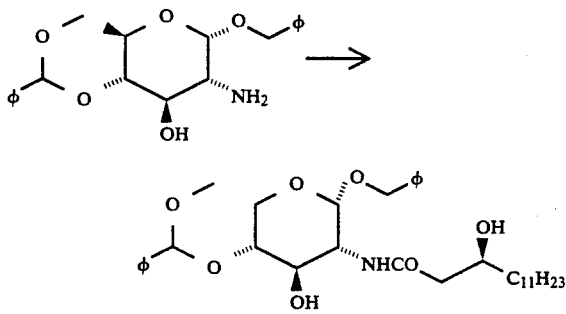

(3S)-Hydroxymyristic acid (50 g) was dissolved into tetrahydrofuran (50 ml) under an atmosphere of argon. After to this solution was added triethylamine (29.3 ml), to the mixture was added gradually pivaloyl chloride (19.5 ml) keeping the temperature below 10° C. After stirred for 30 min at same temperature, to the mixture was added a solution of benzyl 2-amino-4,6O-benzylidene-2-deoxy-α-D-glucopyranoside (50 g) in THF (500 ml) and hexamethylphosphoramide (40 ml) keeping the temperature below 20° C. After stirred for 4 h at room temperature, the resulting precipitate was removed by filtration from the mixture. After the filtrate was concentrated under reduced pressure, the obtained residue was dissolved into acetonitrile (800 ml), purified by recrystallization to give the title compound (78.1 g) having the following physical data.

Yield: 95%;
mp.: 168°–169° C.;
TLC: Rf 0.5 (methylene chloride:methanol=10:1);
NMR: δ7.25 (m, 2H), 7.20 (m, 8H), 6.20 (d, 1H), 5.3 (s, 1H), 4.95 (d, 1H), 4.75 (d, 1H), 4.5 (d, 1H), 4.15 (m, 2H), 3.75 (m, 5H), 3.2 (br, 1H), 3.1 (br, 1H), 2.3 (m, 2H), 0.9 (t, 3H).

REFERENCE EXAMPLE 2

Preparation of benzyl 2-[(3S)-(9-phenylnonanoyloxy)tetradecanoyl]amino-3-O-(9-phenylnonanoyl)-4,6-O-benzylidene-2-deoxy-α-D-glucopyranoside

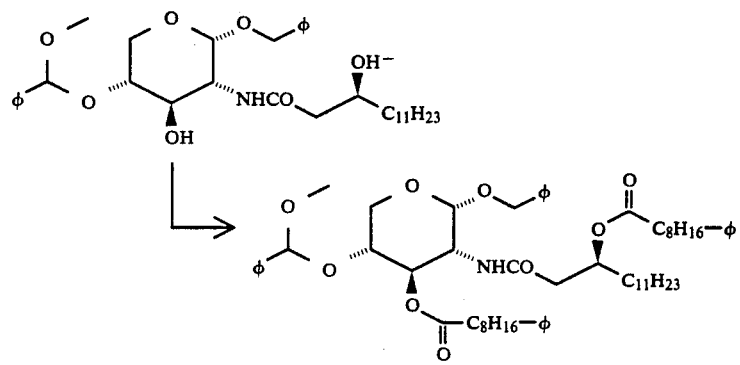

A mixture of the compound prepared in reference example 1 (78.1 g) and 9-phenylnonanic acid (68.5 g) was dissolved into methylene chloride (700 ml) under an atmosphere of argon. After to this solution were successively added 2-chloro-1-methylpyridinium iodide (85.0 g), dimethylaminopyridine (16.2 g) and triethylamine (83.3 ml), the mixture was stirred overnight at room temperature. After the reaction was completed, to the mixture was added methanol (3 ml). After stirred for 20 min, the mixture was concentrated under reduced pressure. The residue was dissolved into ethyl acetate (500 ml), washed with water, dried over anhydrous magnesium sulfate, and evaporated. The residue was dissolved into isopropanol (700 ml), purified by recrystallization to give the title compound (72.5 g) having the following physical data.

Yield: 55%;
mp.: 74°–75° C.;
TLC: Rf 0.59 (hexane:ethyl acetate=3:1);
NMR: δ7.4–7.0 (m, 20H), 6.1 (d, 1H), 5.5 (s, 1H), 5.35 (t, 1H), 5.15 (br, 1H), 4.95 (d, 1H), 4.75 (d, 1H), 4.5 (d, 1H), 4.3 (m, 2H), 3.8 (m, 3H), 2.6 (m, 4H), 2.3 (m, 6H), 0.9 (t, 3H)

REFERENCE EXAMPLE 2(a)

Preparation of benzyl 2-[(3S)-(9-phenylnonanoyloxy)tetradecanoyl]amino-3-O-(9-phenylnonanoyl)-4,6-O-benzylidene-2-deoxy-α-D-glucopyranoside.

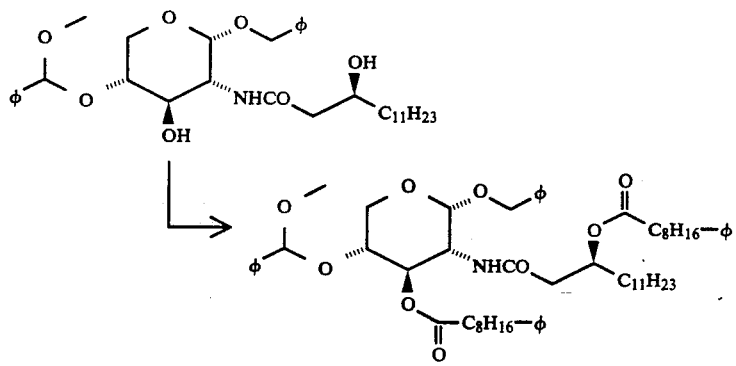

To a solution of N,N,N',N'-tetramethylurea (1394 mg) in methylene chloride (4 ml) was added oxalyl chloride (0.52 ml) under an atmosphere of argon. After stirred for 2h at 65° C., the mixture was cooled to room temperature. To this solution were successively added 9-phenylnonanic acid (515 mg), pyridine (1.6 ml), acetonitrile (20 ml) and the compound prepared in reference example 1 (583 mg). The reaction mixture was stirred overnight at room temperature. After the reaction was completed, the mixture was concentrated under reduced pressure. The residue was dissolved into ethyl acetate, washed with water, an aqueous solution of sodium bicarbonate, successively, dried over anhydrous magnesium sulfate, and evaporated. The residue was purified by silica gel column chromatography (hexane: chloroform=1:2) to give the title compound (660 mg) having the same physical data that the compound prepared in reference example 2 has.

Yield: 65.0%;

REFERENCE EXAMPLE 2(b)

Preparation of benzyl 2-[(3S)-(9-phenylnonanoyloxy)tetradecanoyl]amino-3-O-(9-phenylnonanoyl)-4,6-O-benzylidene-2-deoxy-α-D-glucopyranoside A mixture of the compound prepared in reference example 1 (1.89 g), 9-phenylnonanic acid (1.60 g) and 1,3-dimethyl-2-chloroimidazolinium chloride was dissolved into methylene chloride (15 ml) under an atmosphere of argon. To this solution was added dropwise pyridine (1.54 ml) over a 5 min period at room temperature. The reaction mixture was stirred overnight at room temperature. After the reaction was completed, to the mixture was added hexane. The solution was washed with an aqueous solution of sodium bicarbonate, water and an aqueous solution of copper sulfate, successively, dried over anhydrous magnesium sulfate, and evaporated. The residue was purified by silica gel column chromatography (methylene chloride: ethyl acetate=20:1) to give the title compound (2.72 g) having the same physical data that the compound prepared in reference example 2 has.

Yield: 82.4%;

EXAMPLE 1

Preparation of 2-[(3S)-9-phenylnonanoyloxy)tetradecanoyl]amino-3-O-(9-phenylnonanoyl)-2-deoxy-D-glucopyranoside

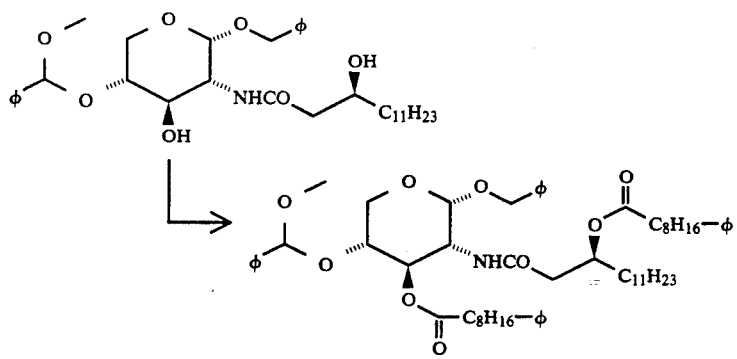

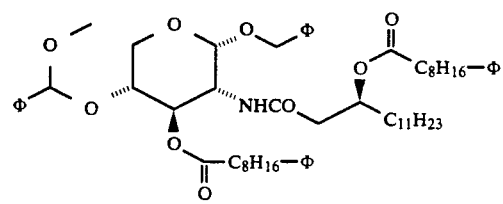

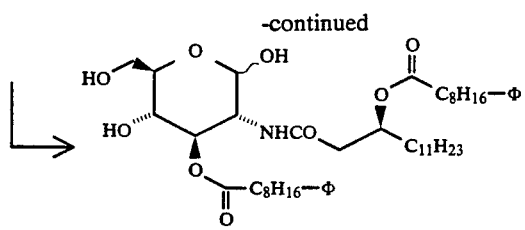

A mixture of the compound prepared in reference example 2, 2(a) or 2(b) (20.3 g), sodium tetrafluoroborate (9.88 g), an aqueous solution of tetrafluoroboric acid (42% containing, 2.8 ml), palladium on activated carbon (6 g) and dimethoxyethane (100 ml) was stirred for 15 h at ordinary pressure and temperature under an atmosphere of hydrogen. After the reaction was completed, the catalyst was removed by filtration. The catalyst was washed with ethyl acetate. To the all filtrate was gradually added an aqueous solution of sodium bicarbonate (0.75M, 50 ml). The mixture was diluted with ethyl acetate, and separated. The organic layer was dried over anhydrous magnesium sulfate, and evaporated to give the title compound of crude product (16.1 g).

TLC: Rf 0.28 (methylene chloride: ethanol=20:1);

NMR (CDCl$_3$+CD$_3$OD): δ7.25-7.0 (m, 10H), 6.5 (d, 1H), 5.1 (m, 3H), 4.0-3.3 (m, 7H), 2.5 (t, 4H), 2.3 (m, 6H), 0.8 (t, 3H).

EXAMPLE 1(a)

Preparation of 2-[(3S)-9-phenylnonanoyloxy)tetradecanoyl]amino-3-O-(9-phenylnonanoyl)-2-deoxy-D-glucopyranoside To a solution of the compound prepared in reference example 2, 2(a) or 2(b) (623.7 g) in dioxane (1.8 l) were successively added sodium tetrafluoroborate (301.4 g), an aqueous solution of tetrafluoroboric acid (42% containing, 87 ml) and palladium on activated carbon (187 g). The mixture was stirred overnight at ordinary pressure and temperature under an atmosphere of hydrogen. After the reaction was completed, the mixture was added an aqueous solution of sodium bicarbonate (2M, 600 ml), and stirred. The mixture was filtered through Celite (registered trade mark), and concentrated under reduced pressure. The residue was purified by silica gel column chromatography (chloroform:methanol=30:1) to give the title compound (349 g) having the same physical data that the compound prepared in reference example 1 has.

Yield 66.5%

REFERENCE EXAMPLE 3

Preparation of 2-[(3S)-9-phenylnonanoyl)tetradecanoyl]amino-3-O-(9-phenylnonanoyl)-6-O-t-dimethylsilyl-2-deoxy-D-glucopyranoside

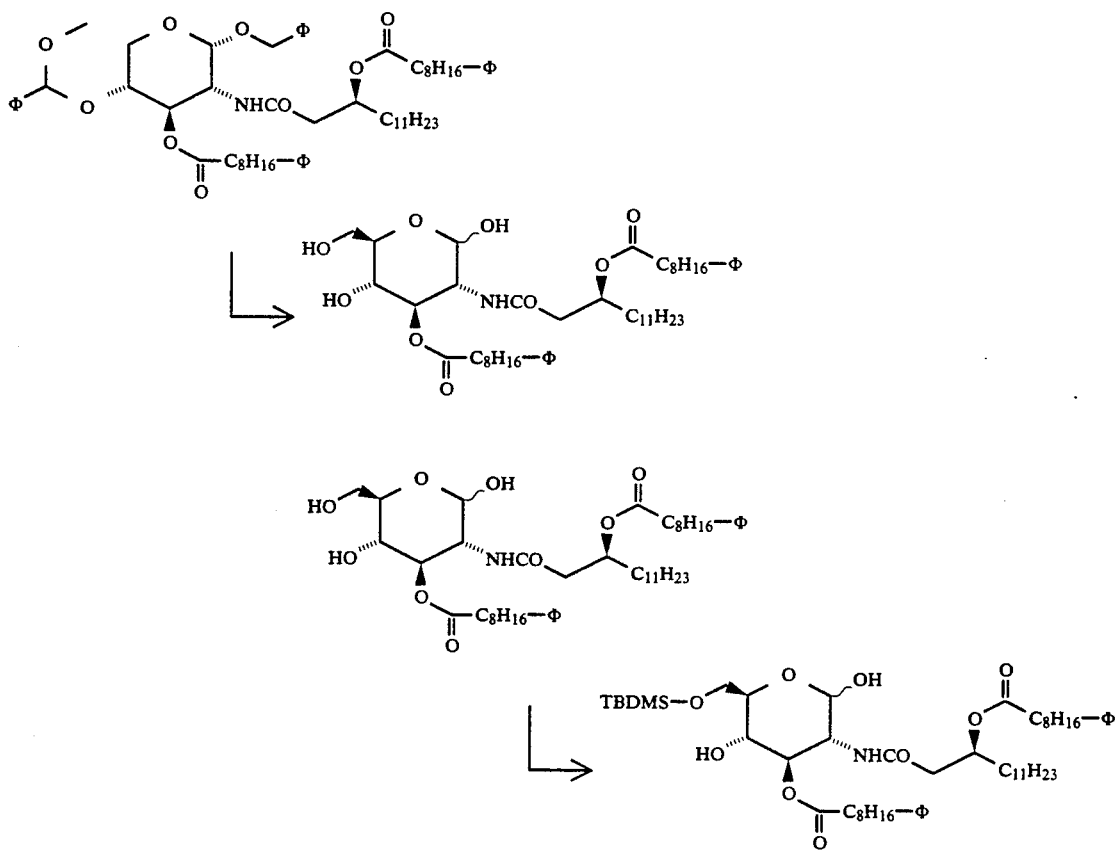

A compound prepared in example 1 or 1(a) (274.2 g) was dissolved into pyridine (1.6 liter) under an atmosphere of argon. To the reaction mixture were successively added t-butyldimethylsilyl chloride (59.1 g) and dimethylaminopyridine (16 g), and stirred for 3 h at room temperature. After the reaction was completed, to the mixture was added methanol (40 ml) and concentrated under reduced pressure. The residue was purified by silica gel column chromatography (chloroform:methanol=50:1) to give the title compound (307 g) having the following physical data.

Yield: 98.5%;
TLC: Rf 0.51 (methylene chloride:ethanol=20:1);
NMR: $\delta$7.25-7.0 (m, 10H), 6.1 (d, 1H), 5.1 (m, 3H), 2.6 (t, 4H), 2.3 (m, 6H), 0.9 (m, 12H), 0.1 (s, 6H)

REFERENCE EXAMPLE 4

Preparation of sodium 2-[(3S)-(9-phenylnonanoyloxy)tetradecanoyl]amino-3-O-(9-phenylnonanoyl)-4-O-sulfo-6-O-t-butyldimethylsilyl-2-deoxy-D-glucopyranose

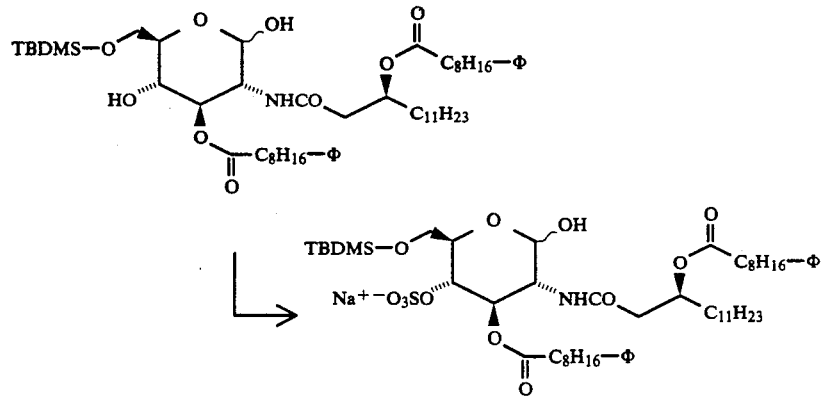

A compound prepared in reference example 3 (265.2 g) was dissolved into pyridine (1.41) under an atmosphere of argon. To this solution was added sulfur trioxide pyridine complex (75.3 g) at room temperature, and stirred for 1 h. After the reaction was completed, to the mixture was added ethanol (150 ml), and stirred for 30 min. The reaction mixture was concentrated under reduced pressure. The residue was dissolved into ethyl acetate (3 liter). The solution was salt-exchanged with 5% aqueous solution of sodium acetate, and eraporated to give the title compound having the following physical data.

TLC: Rf 0.05 (methylene chloride:ethanol=20:1).

REFERENCE EXAMPLE 4(a)

Preparation of sodium 2-[(3S)-9-phenylnonanoyloxy)tetradecanoyl]amino-3-O-(9-phenylnonanoyl)-4-O-sulfo-6-O-t-butyldimethylsilyl-2-deoxy-D-glucopyranose

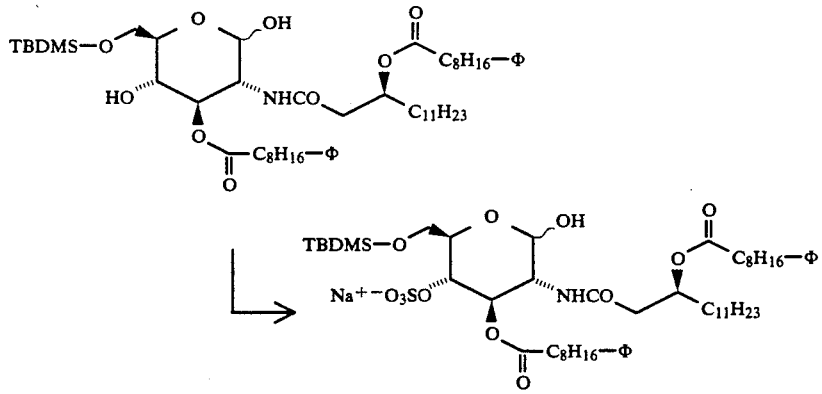

A compound prepared in reference example 3 (500 mg) was dissolved into pyridine (6 ml) under an atmosphere of argon. To this solution was added sulfur trioxide triethylamine complex (330 mg), and stirred for 2 h at 50° C. After the reaction was completed, to the mixture was added ethanol (0.4 ml), and stirred for 10 min. After the reaction was completed, the solution was concentrated under reduced pressure. The residue was dissolved into ethyl acetate, salt-exchanged twice with an aqueous solution of sodium acetate. The organic layer was concentrated under reduced pressure to give title compound (crude product 184 mg) having the following physical data.

TLC: Rf 0.08 (methylene chloride:ethanol=20:1)

EXAMPLE 2

Preparation of sodium 2-[(3S)-(9-phenylnonanoyloxy)tetradecanoyl]amino-3-O-(9-phenylnonanoyl)-4-O-sulfo-2-deoxy-D-glucopyranose

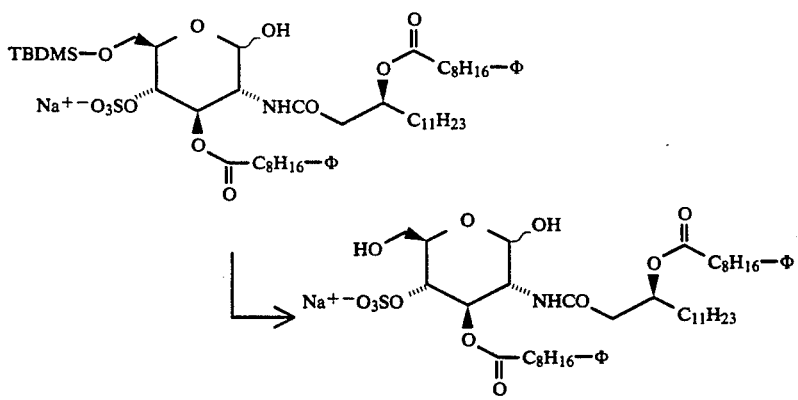

To a solution of the compound prepared in reference example 4 or 4(a) in ethanol (600 ml) were successively added acetic acid (600 ml) and water (200 ml), and stirred for 18 h at room temperature. After the reaction was completed, the mixture was concentrated under reduced pressure. The residue was dissolved into chloroform, and salt-exchanged with 5% aqueous solution of sodium bicarbonate. The organic layer was dried over anhydrous sodium sulfate, and evaporated to give the crude product (233 g). The crude product was recrystallized twice from ethanol (600 ml) to give the title compound (130 g) having the following physical data.

Yield 50% (overall yield from the compound prepared in reference example 3);

mp.: 149°–150° C.;

TLC: Rf 0.45 (chloroform:methanol:water = 100:3:2);

NMR (CDCl$_3$+CD$_3$OD): δ7.25–7.00 (m, 10H), 5.23 (t, 1H), 5.15–4.98 (m, 2H), 4.38 (t, 1H), 2.50 (t, 4H), 2.20 (t, 4H), 0.79 (t, 3H).

REFERENCE EXAMPLE 5

Preparation of the mixture salt of calcium, sodium and magnesium of 2-deoxy-2-[(3S)-9-phenyl-nonanoyloxy)tetradecanoyl]amino-3-O-(9-phenyl-nonanoyl)-4-O-sulfo-D-glucopyranose

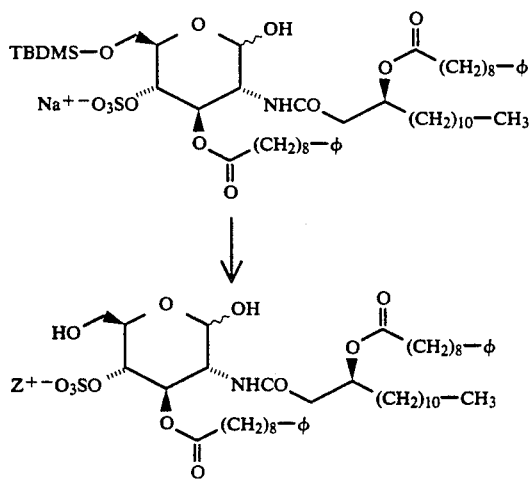

Z$^+$ is mixture of sodium, calcium and magnesium

To a solution of the compound prepared in reference example 4 (1042 g) in ethanol (3 liter) were successively added acetic acid (3 liter) and water (1 liter), and stirred for 18 h at room temperature. After the reaction was completed, the mixture was concentrated under reduced pressure. After this solution was neutralized by addition of a saturated aqueous solution of sodium bicarbonate, the mixture was extracted with chloroform-methanol (1:1) (14 liter). The extract was dried over anhydrous magnesium sulfate, and evaporated. The residue was purified by silica gel column chromatography (first; ethyl acetate:methanol:water = 100:10:1; second by; chloroform:methanol:water = 200:20:1→100:20:1) to give the title mixture of salt (568 g) having the following physical data.

TLC: Rf 0.21 (ethyl acetate:methanol:water = 100:10:1).

EXAMPLE 3

Preparation of sodium 2-deoxy-2-[(3S)-(9-phenyl-nonanoyloxy)tetradecanoyl]amino-3-O-(9-phenyl-nonanoyl)-4-O-sulfo-D-glucopyranose

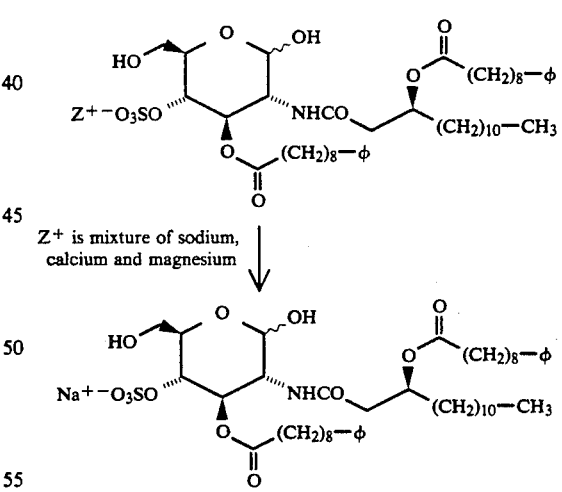

Z$^+$ is mixture of sodium, calcium and magnesium

A cation-exchange resin (—SO$_3$Na type) (6 liter) was successively washed with water (5 liter) and methanol (18 liter). A solution of the mixture of salt prepared in reference example 5 (568 g) in methanol (2 liter) was developed on column packed with above resin. The column was eluted with methanol (8 liter) to give crude product (600 g). The crude product (300 g) was developed on reversed phase silica gel, and eluted with methanol-water (7:1; 400 liter) and methanol-water (9:1; 10 liter). The elution was concentrated under reduced pressure. The residue was added ethanol, and concentrated under reduced pressure. To the residue was dissolved into a mixture of chloroform-methanol (2 liter+0.6 liter), and dried over anhydrous sodium sulfate (0.5 kg). After concentrated under reduced pressure to remove solvent, the residue was dissolved into a mixture of ethanol-methanol (1.5 l+0.5 l), and treated with activated carbon (13 g). The filtrate was concentrated to give the crude product (225 g). After the residue was dissolved into ethanol (550 ml) with heating, this solution was permitted to stand for 24 h at room temperature. The precipitated crystal was collected by filtration, and washed with ethanol to give the title compound (187 g) having the following physical data.

TLC: Rf 0.40 (ethyl acetate:acetic acid:-water=10:2:1);

mp.: 142°-144° C. (decomposition);

IR(KBr): ν3431, 2927, 2853, 1713, 1671, 1526, 1467, 1457, 1250, 1134, 1058, 997, 821, 774, 698, 608 cm$^{-1}$;

NMR (CD$_3$OD): δ7.17 (m, 10H), 5.35 (dd, 1H), 5.13(q, 1H), 5.09 (d, 1H), 4.37(t, 1H), 4.14 (dd, 1H), 2.59 (t, 4H), 2.28 (m, 6H), 0.88 (t, 3H).

REFERENCE EXAMPLE 6

Preparation of calcium 2-deoxy-2-[(3S)-(9-phenylnonanoyloxy)tetradecanoyl]amino-3-O-(9-phenylnonanoyl)-4-O-sulfo-D-glucopyranose of the gel thus obtained and 10% aqueous solution of calcium chloride (15 liter) was stirred overnight at room temperature, and washed with water. Further a mixture of the gel thus obtained and 10% aqueous solution of calcium chloride (15 liter) was stirred for 8 h at room temperature, and washed with water. The gel thus obtained was packed with column, and flowed with 10% aqueous solution of calcium chloride (15 liter), and washed with water, ethanol and hexane, successively. The gel was centrifuged, and air-dried for 1 day at room temperature, dried over for 42 h at 105° C., and dried over phosphorus pentoxide as drying agent for 4 h. A mixture of salt prepared in reference example 5 (0.7 g) was placed on column packed with above gel (140 ml). The column was eluted with a mixture of chloroform-methanol (30:1→20:1→10:1). The elution was concentrated under reduced pressure. Thus obtained residue was suspended in the mixture of ethanol-water (4 ml:30 ml), and lyophilized, dried over phosphorus pentoxide as drying agent to give the title compound (0.58 g).

EXAMPLE 4

Preparation of tris(hydroxymethyl)methylammonium 2-deoxy-2-[(3S)-(9-phenylnonanoyloxy)tetradecanoyl]amino-3-O-(9-phenylnonanoyl)-4-O-sulfo-D-glucopyranose

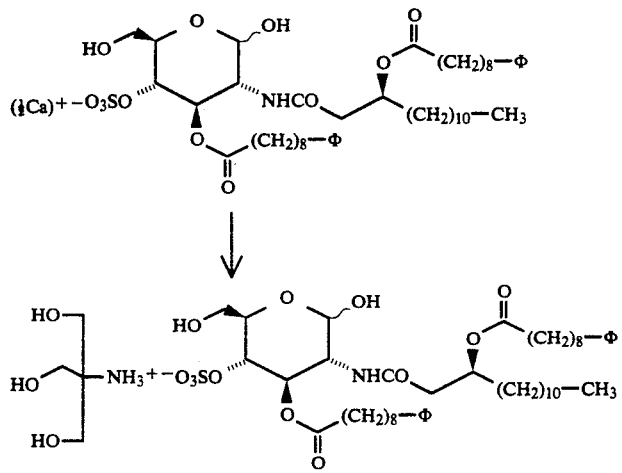

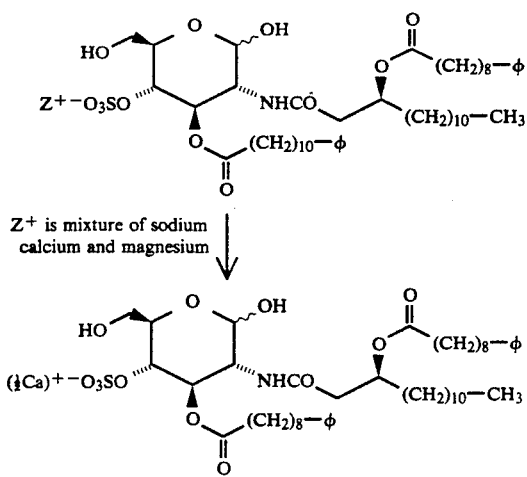

Z$^+$ is mixture of sodium calcium and magnesium

A mixture of silica gel (2 kg) and 15% aqueous solution of calcium chloride (10 liter) was stirred for 3.5 h at room temperature, and washed with water. A mixture After a cation-exchange resin (—SO$_3$H type) (100 ml) was successively washed with water and ethanol, flowed with 10% aqueous solution of tris(hydroxymethyl)aminomethane (500 ml). After the resin was washed with water until this solution became neutrality, and replaced with methanol. After a calcium salt prepared in reference example 6 (1.1 g) was placed on column, and eluted with methanol. The elution was concentrated under reduced pressure. The residue was carried out the same procedure in above. After thus obtained residue was dissolved into ethanol (4 ml), and added water (20 ml), and lyophilized to give the title compound (1.11 g) having the following physical data.

FAB-Mass: 1160 (M+Tris H)$^+$;

IR(KBr): ν3361, 2927, 2854, 1734, 1656, 1542, 1497, 1467, 1256, 1126, 1054, 995, 821, 748, 698, 602 cm$^{-1}$;

NMR (CDCl$_3$+CD$_3$OD): δ7.35-7.1 (m, 10H), 5.3 (dd, 1H), 5.1 (m, 2H), 4.4 (t, 1H), 4.1 (dd, 1H), 3.7 (s, 6H), 2.6 (t, 4H), 2.35 (m, 6H), 0.9 (t, 3H)

EXAMPLE 5

Preparation of sodium 2-deoxy-2-[(3S)-(9-phenyl-nonanoyloxy)tetradecanoyl]amino-3-O-(9-phenyl-nonanoyl)-4-O-sulfo-D-glucopyranose

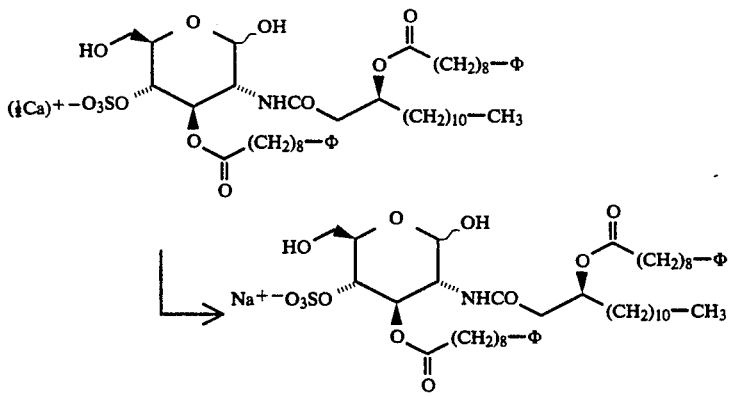

By the same procedure as example 3 by using calcium salt prepared in reference example 6, the title compound was given. Physical data of the compound thus obtained was identified with example 3.

EXAMPLE 6

Preparation of sodium 2-deoxy-2-[(3S)-(9-phenyl-nonanoyloxy)tetradecanoyl]amino-3-O-(9-phenyl-nonanoyl)-4-O-sulfo-α-D-glucopyranose

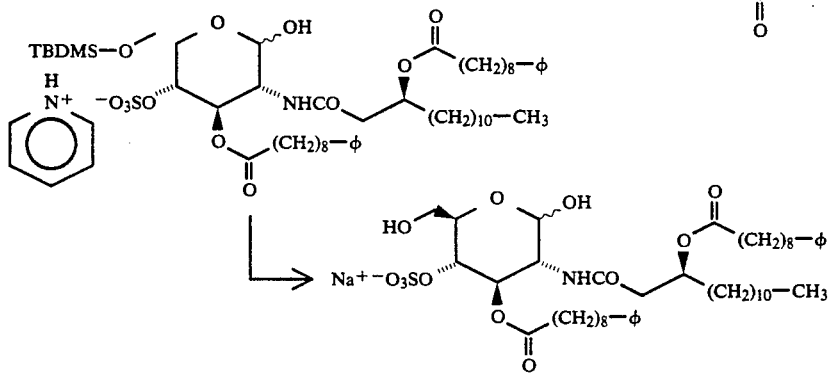

By the same procedure as example 2 by using pyridinium 2-deoxy-2-[(3S)-(9-phenylnonanoyloxy)tetradecanoyl]amino-3-O-(9-phenylnonanoyl)-4-O-sulfo-6-O-t-butyldimethylsilyl-D-glucopyranose (the compound of reference example 6(c) in the specification of the Japanese Patent Application No. 63-179885, the description was acid of free, but the compound was, in fact, salt with pyridine, 56 g), the title compound (26 g) was given. Physical data of the compound thus obtained was identified with example 2.

FORMULATION EXAMPLE 1

The following componets were admixed in conventional manner. The solution was steilized in conventional manner, placed 2 ml portions into 10 ml ampoules to obtain 100 ampoules each containing 100 mg of the active ingredient.

Sodium 2-deoxy-2-[(3S)-(9-phenylnonanoyloxy)tetradecanoyl]amino-3-O-(9-phenylnonanoyl)-4-O-sulfo-α-D-glucopyranose - - - 10 g 55% Ethanol - - - 200 ml While the invention has been described in detail and with reference to specific examples thereof, it will be apparent to one skilled in the art that various changes and modifications can be made therein without departing from the spirit and scope thereof.

What we claim is:

1. A glucopyranose derivative of the formula (II)

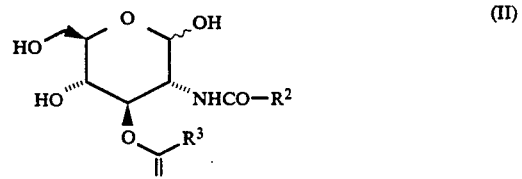

(II)

wherein $R^2$ is

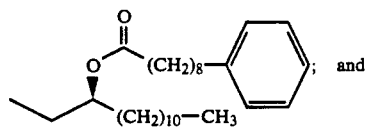; and wherein $R^3$ is

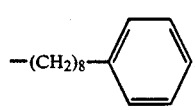.

* * * * *